(12) United States Patent
Barton et al.

(10) Patent No.: US 6,268,217 B1
(45) Date of Patent: Jul. 31, 2001

(54) ERYTHROCYTE PARAMETERS IN HEMOCHROMATOSIS

(76) Inventors: James C. Barton, 3828 Brook Hollow La., Birmingham, AL (US) 35243; Luigi F. Bertoli, 26,2700 Arlington Ave. South, Birmingham, AL (US) 35206; Barry E. Rothenberg, 149 12$^{th}$ St., Delmar, CA (US) 92014

(*) Notice: Subject to any disclaimer, the term of this patent is extended or adjusted under 35 U.S.C. 154(b) by 0 days.

(21) Appl. No.: 09/439,965

(22) Filed: Nov. 12, 1999

(51) Int. Cl.$^7$ ...................................................... G01N 33/72
(52) U.S. Cl. ................................ 436/66; 436/63; 436/70; 436/10
(58) Field of Search ................................. 436/63, 66, 70, 436/10; 435/2, 29, 30

(56) References Cited

U.S. PATENT DOCUMENTS 5,674,681 * 10/1997 Rothenberg .............................. 435/6

OTHER PUBLICATIONS

Khanh et al. *Journal of Tropical Pediatrics,* vol. 36, pp. 43–45, Feb. 1990.*

Barton et al. *Blood*, vol. 92, No. 10, Suppl. 1 Part 1–2, pp. 12B, Nov. 15, 1998.*

* cited by examiner

*Primary Examiner*—Maureen M. Wallenhorst
(74) *Attorney, Agent, or Firm*—Ingrid A. Beattie; Mintz, Levin, Cohn, Ferris, Glovsky and Popep, P.C.

(57) ABSTRACT

The invention provides a method of diagnosing hemochromatosis or a predisposition thereto by detecting an increase in erythrocyte parameters such as mean corpuscular volume or mean corpuscular hemoglobin compared to normal individuals unaffected by hemochromatosis.

18 Claims, 1 Drawing Sheet

ERYTHROCYTE PARAMETERS IN HEMOCHROMATOSIS

BACKGROUND OF THE INVENTION

The invention relates to diagnosis of iron disorders.

Hemochromatosis is a common hereditary disorder that affects approximately 0.5% of persons of western European descent. In various populations, 60%–100% of cases are attributable to homozygosity for a missense mutation (cDNA nucleotide 845 G6A; C282Y) in HFE, a major histocompatibility class I gene on chromosome 6p. Some patients are compound heterozygotes for C282Y and another HFE allele (cDNA nucleotide 187 C6G; H63D), or are H63D homozygotes. However, C282Y and H63D are not known to occur on the same chromosome. Other persons with a hemochromatosis phenotype are homozygous for H63D, are heterozygous for C282Y or H63D, or are presumed to have an HFE or other mutation that is not presently detectable (wild-type; wt/wt). Regardless of HFE genotype, persons with a hemochromatosis phenotype usually have increased iron saturation of plasma transferrin, typically absorb increased quantities of iron, and often develop multisystem disease due to iron overload.

SUMMARY OF THE INVENTION

The invention is based on the discovery that peripheral blood erythrocyte parameters in hemochromatosis patients or those at risk of developing hemochromatosis is distinguished from the erythrocyte parameters of normal individuals. Hemoglobin (Hb), hematocrit (Hct), mean corpuscular volume (MCV), mean corpuscular hemoglobin (MCH), and mean corpuscular hemoglobin concentration (MNCHC) values were significantly higher in hemochromatosis patients compared to normal control individuals. Accordingly, the invention provides a methods of diagnosing hemochromatosis or a predisposition thereto by detecting altered erythrocyte parameters.

A method of diagnosing hemochromatosis or a predisposition thereto in a mammal is carried out by determining the mean corpuscular volume (MCV) value of a blood sample from the mammal. An an increase of at least 5% compared to a normal control value indicates that said mammal has hemochromatosis or is predisposed to developing hemochromatosis. A normal control value or range is one obtained by testing an individual or pool of individuals who are wt/wt. Individuals used to determine a normal control value or range are neither homozygous nor heterozygous for a genetic mutation associated with hemochromatosis such as C282Y or H63D of the HFE gene. Preferably, the increase is at least 7%, more preferably at least 7.5%, more preferably at least 8%, more preferably at least 9%, and most preferably at least 10% higher than a normal control value or range. Preferably, the erythrocyte profile of the tested individual does not indicate an anemic condition. For example, a red blood cell count (RBC), hematocrit (Hct), or hemoglobin concentration (Hb) should be within a normal range but the MCV value is elevated compared to a normal value or range to indicate a diagnosis of hemochromatosis.

A method of diagnosing hemochromatosis or a predisposition thereto in a mammal is also carried out by determining that the MCV value of a blood sample from the mammal is at least 80 fL. Preferably, the value is at least 85 fL, and more preferably the value is in the range of 90–102 fL. An erythrocyte profile of hemochromatosis is distinguished from one previously thought to be associated with a hepatic disease in that the inventive profile diagnostic of hemochromatosis does not include an erythrocyte parameter, e.g., RBC, Hct, or Hb, which indicates anemia. Hemochromatosis is also diagnosed by determining the mean corpuscular hemoglobin (MCH) value, mean corpuscular hemoglobin concentration (MCHC), Hb, or Hct of a blood sample from the mammal. An increase of at least 5% (preferably at least 7%, more preferably at least 7.5%, more preferably at least 8%, more preferably at least 9%, and most preferably at least 10%) compared to a normal control value indicates that said mammal has hemochromatosis or is predisposed to developing hemochromatosis. As above, the erythrocyte profile indicative of a diagnosis of hemochromatosis does not include a parameter such as RBC, Hct, or Hb which indicates an anemic condition. Hemochromatosis is diagnosed by determining that the MCH value of a blood sample from the mammal is at least 26 pg. More preferably, the value is at least 28 pg, such as a value in the range of 30–35 pg.

The present method overcomes the insensitivity of the prior art because the standard value ranges of Hb, Hct, MCV, and MCH are not true "normal ranges" because at least 25% of the population contains at least one mutation associated with hemochromatosis. The data reported herein indicates that the inclusion of such individuals in the determination of the standard ranges of values results in ranges that are not reflective of a normal control, but are approximately 5–10% higher. The diagnostic methods of the invention are used to properly use information already obtained from standard hematological tests and extract the maximum information from the red blood cell indices.

The methods of measuring erythrocyte parameters are well known, but the interpretation of the results to diagnose hemochromatosis is new. Hemochromatosis was not diagnosed using the previous assays because the values of hemochromatosis patients would fall into the "normal ranges". However, the normal ranges of the prior art were skewed because of the inadvertent inclusion of individuals which are homozygous or heterozygous for hemochromatosis-associated mutations (and which elevated Hb, Hct, MCV, or MCH values compared to individuals without a hemochromatosis-associated mutation Other features and advantages of the invention will be apparent from the following description of the preferred embodiments thereof, and from the claims.

DESCRIPTION OF THE PREFERRED EMBODIMENTS

Figure 1:
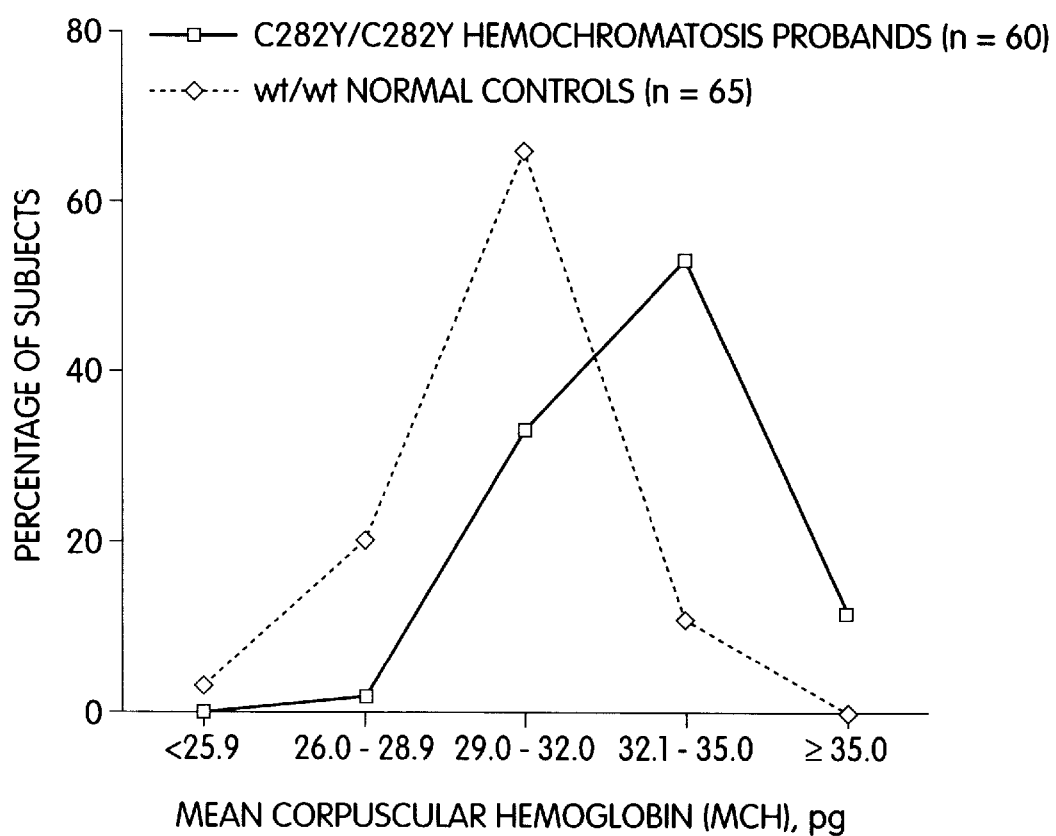
FIG. 1 is a bar graph showing the frequency of mean corpuscular hemoglobin values in C282Y/C282Y probands and wt/wt controls.

Peripheral blood erythrocyte parameters and HFE genotypes in 94 hemochromatosis probands and 132 Caucasian normal controls were evaluated. Mean red blood cell (RBC) counts in probands and controls were not significantly different. However, mean values of Hb, Hct, MCV, MCH, and MCHC were significantly higher (e.g., at least 5% higher) in C282Y/C282Y probands (n=60) than in wild-type (wt/wt) controls (n=65). Probands with other HFE genotypes also had increased mean erythrocyte parameters (other than RBC). A proband is the first individual in a family identified to be affected by hemochromatosis.

Forward and Peripheral blood smears prepared before therapeutic phlebotomy to remove iron revealed that erthocytes in many probands had increased diameters and were well-filled with hemoglobin. Erythrocyte parameters were similar in C282Y/C282Y probands with and without hepatomegaly, elevated serum concentrations of hepatic enzymes, hepatic cirrhosis, diabetes mellitus, arthropathy, or hypogonadism. Among C282Y/C282Y probands, significantly greater values of MCV (but not other erythrocyte parameters) occurred among those who had transferrin saturation values of at least 75% or iron overload at diagnosis. After iron depletion, the mean MCV, MCH, and MCHC values of C282Y/C282Y probands decreased, but remained significantly greater than values in wt/wt controls. Mean values of pre-phlebotomy MCH and MCHC were lower in HLA-A3-positive than in HLA-A3-negative C282Y/C282Y probands. These data indicate that increased values of mean Hb, Hct, MCV, MCH, and MCHC in hemochromatosis probands are due to increased iron uptake and hemoglobin synthesis by immature erythroid cells.

Red blood cell (RBC), Hb, Hct, MCV, MCH, MCHC parameters are measured using methods well known in the art of hematology, e.g, using an automated analyzer such as the Cell-Dyne 1700. Other analyzers such as a Model S particle analyzer (U.S. Pat. No. 3,549,994) are widely used to generate patient hematological data. MCV is directly detected or is derived as the quotient of hematocrit and red blood cell count, i.e., MCV=HCT/RBC. Similarly, MCH is the quotient of haemoglobin and red blood cell count, i.e., MCH=Hb/RBC.

PCV is the ratio of the volume of packed red cells to the total volume. For example, an electric counter makes a direct measurement of the red cell count (RBC/pL) and mean red cell volume:

$$MCV(fL) = \frac{PCV(L/L)}{RBC(\mu L) \times 10^{-9}}$$

$$MCHC(g/dL) = \frac{Hb(g/dL)}{PCV(L/L)}$$

$$MCH(pg) = \frac{Hb(g/dL)}{(RBC/\mu L) \times 10^{-7}}$$

The hemochromatosis index described herein provides a highly informative discriminant between hepatic disease and hemochromatosis, such two conditions having very different prognoses, but yet frequently being confused during diagnosis using current diagnostic indices. The data described herein indicates that individuals with a RBC, Hct or Hb level that is not indicative of an anemic condition, but having a MCV, MCH, or Hb level that is at least 5% above the upper reference range of a standard normal value is diagnostic of hemochromatosis or a predisposition thereof For example, an individual with a RBC range between $4.20–6.30 \times 10^6$ $\mu L$ (or other erythrocyte parameters consistent with a nonanemic condition) but with an elevated MCV, MCH, Hct or Hb level that is elevated is identified as having hemochromatosis or at risk of developing the condition.

Patients and Methods

Selection of Hemochromatosis Probands and Normal Control Volunteers

All persons who participated were Caucasians at least 18 years of age. Hemochromatosis probands were identified during routine medical care delivery who had completed iron depletion with therapeutic phlebotomy; probands with complications of iron overload (hepatic cirrhosis, diabetes mellitus, hemochromatosis-associated arthropathy, or hypogonadotrophic hypogonadism) were not excluded. At the time of diagnosis of hemochromatosis, each proband had a normal serum folate concentration, serum vitamin B12 concentration, and thyroid profile. Volunteer normal control subjects unrelated to our hemochromatosis probands were recruited from the general population. Probands and control subjects who had alcoholism, increased erythrocyte mass, anemia other than that attributed to complications of iron overload, unexplained reticulocytosis, marrow infiltrative disease, leukemia or other malignancy, evidence of cold agglutinins or cryoglobulins, drug use associated with erythrocyte abnormalities, pregnancy, malabsorption, vegetarianism, dialysis requirements, transfusion dependency, or inherited disorders of DNA synthesis known to cause macrocytosis, pseudomacrocytosis, or megaloblastosis were excluded.

Diagnosis of Hemochromatosis and Evaluation of Iron Overload

The working diagnostic criterion for hemochromatosis of the American College of Pathologists was used: elevated fasting transferrin saturation (at least 60% males, at least 50% females). In exceptional cases (n=3), transferrin saturation values were not consistently elevated, but otherwise unexplained iron overload consistent with hemochromatosis was demonstrated by analysis of hepatic biopsy specimens and calculation of hepatic iron index. HFE genotyping was not used to establish the diagnosis of hemochromatosis. Iron overload was defined as evidence of systemic iron overload demonstrated by otherwise unexplained elevated serum ferritin concentration (at least 300 ng/mL in men, at least 200 ng/mL in women), increased hepatic iron content determined using hepatic biopsy specimens, or at least 4 g of iron mobilized by phlebotomy. For each proband, the pre-phlebotomy serum transferrin saturation values and serum ferritin concentrations were tabulated, and the units of blood removed by therapeutic phlebotomy (1 unit of blood= 450–500 mL, equivalent to ~200 mg of iron) recorded. Complications of iron overload were assessed using standard methods.

Evaluation of Erythrocyte and other Blood Parameters

Peripheral blood specimens obtained by standard antecubital venipuncture from probands and control subjects were analyzed using a Cell-Dyne7 1200 automated blood counter (Abbott Laboratories, Chicago, Ill.). In probands, serial complete blood counts were obtained before and during iron depletion therapy with phlebotomy. Erythrocyte parameters were also measured in each proband at least three months after the completion of iron depletion therapy at a time when the serum ferritin concentration was 20–50 ng/mL.

Serum iron parameters, serum concentration of hepatic enzymes, and other blood chemistry determinations were performed using automated clinical laboratory methods. Hepatic biopsy specimens were stained with hematoxylin and eosin, acid ferrocyanide, and Masson's trichrome techniques; additional portions of specimens were analyzed for iron content using atomic absorption spectrometry. Peripheral blood smears were prepared with Wright-Giemsa staining, and reticulocytes were enumerated using New Methylene Blue technique. Bone marrow aspirates and biopsy specimens were stained with Wright-Giemsa, hematoxylin and eosin, and acid ferrocyanide technique, as indicated. HFE genotypes and human leukocyte antigen (HLA) immunophenotypes were determined according to standard methods.

Statistical Considerations

The data set consisted of observations on 94 hemochromatosis probands and 132 normal control subjects. There were sufficient numbers of C282Y/C282Y probands (n=60) and normal control subjects (including 65 who had a wt/wt HFE genotype) to permit meaningful analysis of subgroup data. Normal reference ranges for erythrocyte parameters measured using the Cell-Dyne7 1700 supplied by the manufacturer are: erythrocyte (RBC) count $4.20–6.30 \times 10^6$/FL; hemoglobin (Hb) 12.0–18.0 g/dL; hematocrit (Hct) 37.0–51.0%; mean corpuscular volume (MCV), 80.0–97.0 fl; mean corpuscular hemoglobin (MCH) 26.0–32.0 pg; mean corpuscular hemoglobin concentration (MCHC) 31.0–36.0 g/dL; and erythrocyte width distribution RDW) 11.9–14.5%. The reference range for reticulocyte counts in our laboratory is 0.5–1.5%. Descriptive data are presented as percentages or as means±1 S.D. (range). Comparisons were performed using unpaired two-tailed t-test, chi-square analysis, or the correlation coefficient (r), as appropriate. A value of p<0.05 was defined as statistically significant.

General Characteristics of Study Subjects: Hemochromatosis Probands

The mean age of our 94 probands was 51±13 years (range 20–80 years); 58 (61.7%) were men and 36 (38.3%) were women. There was no significant difference in the mean ages of men and women. Fifteen probands (16.0%) had hepatic cirrhosis, 10 (10.6%) had diabetes mellitus, 21 (22.3%) had hemochromatosis-associated arthropathy, and 15 (16.0%) had hypogonadotrophic hypogonadism. Iron overload was more severe and complications of iron overload were more frequent in C282Y/C282Y probands, on the average, than in probands with other HFE genotypes. Frequencies of HFE genotypes among the present probands were similar to those previously reported from unselected hemochromatosis probands from the same geographic area (Table 1).

TABLE 1

HFE Genotype Frequencies in Hemochromatosis Probands and Normal Control Subjects.

| HFE Genotype | Probands (n = 94) | Controls (n = 32) |
|---|---|---|
| C282Y/C282Y | 0.638 | 0 |
| C282Y/wt | 0.128 | 0.182 |
| C282Y/H63D | 0.085 | 0.106 |
| H63D/wt | 0.053 | 0.174 |
| H63C/l63D | 0.032 | 0.045 |
| wt/wt | 0.064 | 0.493 |

*C282Y, cDNA nucleotide 845 G→A; nucleotide 187 C→G; et, wild-type (normal) HFE allele.

Normal Control Subjects

The mean age of our control subjects was 52±15 years (range 18–86 years); 53 (40.2%) were men and 79 (59.8%) were women. There was no significant difference in the mean ages of men and women. Frequencies of HFE genotypes among the control subjects were similar to those previously reported from normal persons from the same geographic area (Table 1).

Erythrocyte Parameters of Study Subjects: Hemochromatosis Probands

Among all probands, males had significantly greater mean values of RBC, Hb, and Hct than women ($4.83\pm0.47\times10^6$/FL vs. $4.36\pm0.42\ 10^6$/FL, 15.8±1.4 g/dL vs. 14.2±1.0 g/dL, and 46.3±4.5% vs. 41.9±3.3% p<0.0001, p<0.0001 and p<0.01, respectively). Mean values of MCV, MCH, and MCHC were not significantly different in men and women. Mean values of RBC, Hb, and Hct were similar among probands of different HFE genotypes, and values in most probands were within the corresponding reference ranges (Table 2). However, 41 (43.6%), 49 (61.7%), and 8 (8.5%) of all probands had values of MCV, MCH, and MCHC, respectively, that were greater than the corresponding reference ranges (Table 2). Peripheral blood smears made before the initiation of therapeutic phlebotomy revealed that erythrocytes in 71.7% of C282Y/C282Y probands and in 64.9% of all probands had mildly or moderately increased diameters and were well-filled with hemoglobin ("thick" macrocytes). Significant numbers of "thin" macrocytes (with or without central "targets"), poikilocytosis, anisocytosis, acanthocytosis, or nuclear hypersegmentation of granulocytes were not observed. Mean RDW values were within the reference range in probands grouped by HFE genotype. Pre-treatment reticulocyte counts in each of 43 probands and bone marrow aspirate and biopsy specimens in each of 8 probands were normal or non-diagnostic.

TABLE 2

Erythrocyte Parameters and Transferrin Saturation Values in 94 Untreated Hemochromatosis Probands.*

| HFE genotype†(n) | RBC, $10_6$/uL | Hb, g/dL | Hct, % | MCV, fL | MCH, pg | Transferrin saturation, % |
|---|---|---|---|---|---|---|
| C282Y/C282Y (60) | 4.57 ± 0.47 (0; 11.7) | 15.0 ± 1.3 (0; 1.7) | 44.2 ± 4.5 (10.0; 3.3) | 97.1 ± 4.8 (51.7; 0) | 32.9 ± 1.8 (65.0; 0) | |
| C282Y/wt (12) | 4.75 ± 0.67 (0; 16.7) | 15.3 ± 2.0 (0; 0) | 44.9 ± 4.8 (8.3; 0) | 95.0 ± 6.5 (33.3; 0) | 32.4 ± 2.0 (50.0; 0) | 69 ± 27 |
| C282Y/H63D (8) | 4.94 ± 0.41 (0; 0) | 16.2 ± 1.2 (0; 0) | 46.1 ± 8.0 (12.5; 0) | 93.6 ± 3.4 (37.5; 0) | 32.6 ± 3.4 (62.5; 0) | 63 ± 5 |
| H63D/wt (5) | 4.87 ± 0.42 (0; 0) | 16.0 ± 1.9 (20.0; 0) | 46.2 ± 5.6 (20.0; 0) | 95.8 ± 3.1 (0; 0) | 33.6 ± 3.1 (80.0; 0) | 55 ± 3 |
| H63D/H63D (3) | 4.84 ± 0.66 | 15.3 ± 2.3 | 45.6 ± 6.0 | 94.3 ± 1.2 | 31.6 ± 1.5 | 59 ± 17 |
| Wt/wt (6) | 4.43 ± 0.28 | 14.7 ± 1.7 | 42.9 ± 4.5 | 95.4 ± 7.1 | 33.2 ± 2.6 | 58 ± 13 |
| All Probands (94) | 4.64 ± 0.50 (1.1; 9.6) | 15.2 ± 1.5 (1.1; 8.5) | 44.5 ± 4.6 (9.6; 3.2) | 96.2 ± 5.5 (43.6; 0) | 32.7 ± 2.2 (61.7; 0) | 76 ± 19 |

*Data are displayed as mean ± 1 S.D. Percentages of probands with values respectively above and below the corresponding reference ranges are shown in parentheses.
†C282Y, cDNA Nucleotide 845 G→A; H63D, cDNA nucleotide 187 C→G; wt, wild-type (normal) HFE allele.

Normal Control Subjects

Men had significantly greater mean values of RBC, Hb, and Hct than women ($5.00\pm0.47\times10^6$/FL vs. $4.39\pm0.40\times10^6$/FL; 15.3×1.4 g/dL vs. 13.3±1.0 g/dL; and 45.4±4.4% vs. 39.8±3.4%; p<0.0001 for each comparison). However, mean values of MCV, MCH, and MCHC were not significantly different in men and women. Mean values of RBC, Hb, and Hct and were similar among normal control subjects of different HFE genotypes, and most values were within the corresponding reference ranges (Table 3). Although the mean values of MCV, MCH, and MCHC were not increased above the corresponding reference ranges in any HFE genotype group, individual values of MCH or MCHC were elevated in some control subjects who inherited the HFE genotypes C282Y/wt or C282Y/H63D (Table 3). Peripheral blood smears did not reveal significant morphologic abnormalities of erythrocytes other than "thick" macrocytes that occurred in some control subjects with HFE genotypes C282Y/wt or C282Y/H63D. Mean RDW values were within the reference range in control subjects grouped by HFE genotype.

Comparisons of Hemochromatosis Probands and wt/wt Normal Control Subjects

Mean values of erythrocyte parameters in probands grouped by HFE genotype (Table 2) were compared with those of wt/wt normal control subjects (Table 3). In C282Y/C282Y probands, these mean values were significantly increased: Hb (p=0.0001), Hct (p=0.008), MCV (p=0.0001), MCH (p=0.0001), and MCHC (p=0.016). Values of MCH in C282Y/C282Y probands and in wt/wt normal control subjects are displayed in FIG. 1. The mean value of MCH was significantly increased in C282Y/H63D probands (p=0.04), and the mean value of MCHC was increased in C282Y/wt probands (p=0.02). Similar trends in mean erythrocyte parameters were also observed in probands with other HFE genotypes (Table 2). However, these values were not significantly different from the respective values in wt/wt normal control subjects, possibly due to the small numbers of probands in these subgroups. Further, the percentages of individual MCHC values above the reference range for our blood cell counter in C282Y/wt, C282Y/H63D, and H63D/wt probands were greater than that of C282Y/C282Y probands. However, these apparent differences may also be attributable to the small numbers of probands in these non-C282Y/C282Y subgroups.

mean of serum ferritin concentrations was marginally greater in men (p=0.05), and the number of units of blood removed by phlebotomy was significantly greater in men than women (37±26 units vs. 21±20 units; p=0.01).

Iron Parameters (Transferrin Saturation, Serum Ferritin Concentration, and Phlebotomy Units)

C282Y/C282Y probands were grouped by values of transferrin saturation at diagnosis (<75% (n=18) and >75% (n=42)); the mean transferrin saturation values in these groups were 61±12% and 92±8%, respectively. In the group with higher mean transferrin saturation, the mean MCV was greater than in those with lower mean transferrin saturation (98.0±4.3% vs. 94.8±5.3%; p=0.02); other mean erythrocyte parameters did not differ significantly between these groups. The mean volume of blood removed by phlebotomy was marginally greater in the high transferrin saturation group (33±25 units vs. 19±20 units, respectively; p=0.05). C282Y/C282Y probands were grouped according to the iron removed by therapeutic phlebotomy (<4 g of iron and >4 g of iron; n=26 and n=34, respectively); mean values of iron parameters were significantly greater in the latter group. Their mean MCV was also greater (98.6±4.1 fL vs. 95.3±4.9 fL, respectively; p=0.006); other mean erythrocyte parameters did not differ significantly between these groups. However, there was no significant correlation (r) between erythrocyte and iron parameters when data from all C282Y/C282Y probands were analyzed. Taken together, these data indicatet that the relationship between erythrocyte and iron parameter data in C282Y/C282Y probands is not a continuous one, but that markedly elevated iron parameters may be associated with unusually high values of MCV.

Complications of Iron Overload

Erythrocyte parameters did not differ significantly in C282Y/C282Y probands with and without hepatomegaly, elevated serum concentrations of hepatic enzymes, or cirrhosis. However, the arithmetic means of the serum ferritin

TABLE 3

Erythrocyte Parameters in 132 Unrelated Normal Control Subjects.*

| HFE genotype†(n) | RBC, $10_6$/uL | Hb, g/dL | Hct, % | MCV, fL | MCH, pg | MCHC, g/dL |
|---|---|---|---|---|---|---|
| C282Y/wt (24) | 4.51 ± 0.43 (0; 20.8) | 14.0 ± 1.5 (0; 4.2) | 41.0 ± 4.2 (0; 16.7) | 31.2 ± 3.0 (0; 0) | 34.0 ± 1.3 (20.8; 0) | 34.1 ± 1.3 (20.8; 0) |
| C282Y/H63D (14) | 4.78 ± 0.65 (0; 21.4) | 14.9 ± 2.2 (0; 0) | 43.7 ± 6.7 (7.1; 14.3) | 91.9 ± 5.3 (14.3; 0) | 31.2 ± 1.7 (0; 0) | 34.0 ± 1.2 (28.6; 35.6) |
| H63D/wt (23) | 4.70 ± 0.48 (0; 13.0) | 14.1 ± 1.5 (4.3; 0) | 42.9 ± 5.1 (4.3; 4.3) | 91.2 ± 5.0 (8.7; 0) | 30.0 ± 2.1 (13.0; 8.7) | 32.9 ± 1.5 (0; 4.3) |
| H63D/H63D (6) | 4.32 ± 0.25 (33.3; 0) | 13.5 ± 0.7 (0; 0) | 40.2 ± 2.8 (0; 0) | 93.1 ± 3.2 (0; 0) | 31.2 ± 1.2 (16.7; 0) | 33.5 ± 1.0 (0; 0) |
| wt/wt (6) | 4.67 ± 0.54 (0; 18.5) | 14.0 ± 1.4 (0; 3.1) | 42.1 ± 4.3 (0; 6.2) | 90.4 ± 3.8 (1.5; 0) | 30.2 ± 1.9 (10.8; 3.1) | 33.3 ± 1.4 (3.1; 9.2) |
| All Controls (132) | 4.64 ± 0.52 (1.5; 17.4) | 14.1 ± 1.5 (0.8; 2.3) | 42.1 ± 4.7 (1.5; 6.8) | 91.0 ± 4.1 (3.8; 0) | 30.4 ± 1.8 (12.1; 3.0) | 33.5 ± 1.4 (8.3; 9.1) |

*Data are displayed as mean ± 1 S.D. Percentages of probands with values respectively above and below the corresponding reference ranges are shown in parentheses.
†C282Y, cDNA nucleotide 845 G→A; H63D, cDNA nucleotide 187 C→G; wt, wild-type (normal) HFE allele.

Relationships of Erythrocyte Parameters to Various Factors in C282Y/C282Y Probands Men had significantly greater mean values of RBC (4.69±0.48×$10^6$/FL vs. 4.41±0.41×$10^6$/FL; p=0.02), Hb (15.4±1.4 g/dL vs. 14.4±0.8 g/dL; p=0.002), and Hct (45.6"4.6% vs. 42.2±3.2%; p=0.002) than women. Mean values of MCV, MCH, MCHC, and transferrin saturation did not differ significantly in men and women. The arithmetic concentration and numbers of units of phlebotomy required to achieve iron depletion were significantly greater in those with hepatic cirrhosis than in those without cirrhosis (2,877±1,769 ng/dL vs. 824±657 ng/dL and 60±32 units vs. 22±17 units; p=0.0001 for each comparison). The occurrence of diabetes mellitus or hemochromatosis-associated arthropathy in C282Y/C282Y probands was not associated with significantly different mean values of erythrocyte parameters than was observed in probands unaffected with these complications. All of our C282Y/C282Y probands with hypogonadotrophic hypogonadism were men; their mean erythrocyte parameters did not differ significantly from those of male C282Y/C282Y probands without hypogonadism.

HLA-A Types

Forty-five C282Y/C282Y probands were positive for HLA-A3 (14 presumed HLA-A3 homozygotes and 31 HLA-A3 heterozygotes); 15 probands did not express HLA-A3. Mean values of pre-phlebotomy MCH and MCHC were lower in HLA-A3-positive than in HLA-A3-negative probands (33.8"1.1 pg vs. 34.5"1.4 pg, p=0.045; and 31.9"2.1 g/dL vs. 33.2"2.1 g/dL, p=0.038, respectively). Other erythrocyte and iron parameters did not differ significantly between HLA-A3-positive and -negative probands.

Effect of Therapeutic Phlebotomy on Erythrocyte Parameters in Hemochromatosis Probands Post-treatment erythrocyte parameters were measured in the same 94 hemochromatosis probands studied before therapeutic phlebotomy. Measurements were made at least three months after completion of iron depletion therapy when the serum ferritin concentration was 20–50 ng/mL (Table 4). In treated C282Y/C282Y probands, the mean RBC value was lower than in wt/wt controls (4.38"0.34× 106/FL probands vs. 4.67"0.54×106/FL controls, p=0.0008). However, mean values of Hb and Hct in C282Y/C282Y probands (Table 4) were similar to those of wt/wt normal control subjects (Table 3). In C282Y/C282Y probands, mean post-treatment values of MCV, MCH, and MCHC remained significantly greater than corresponding measurements in wt/wt normal control subjects (p=0.0001, 0.0001, and 0.008, respectively) (Tables 3 and 4). In probands with other HFE genotypes, similar but less pronounced abnormalities persisted after phlebotomy therapy. Among all 94 probands, post-treatment values of MCV, MCH, and MCHC greater than the upper limit of the corresponding reference ranges were detected in 26 (27.6%), 42 (44.7%), and 4 (4.3%/) probands, respectively.

ing erythrocyte changes in our C282Y/C282Y hemochromatosis probands before or after therapeutic phlebotomy. In hemochromatosis homozygotes, the appearance of marrow erythroid cells, rates of erythrocyte production and destruction, and biochemical analyses of hemoglobin are usually normal. Taken together, these data indicate that increased entry of iron into hemochromatosis erythrocytes is subsequently incorporated into hemoglobin in the cells.

Previously, elevated values of MCV and macrocytosis were thought to be diagnostic of hepatic disease. The results reported herein indicate that this is not correct for hemochromatosis. The profile of erythrocyte parameters described herein as being diagnostic for hemochromatosis differs from the profile indicative of hepatic disease (i.e., anemic conditions). In aggregate, the probands did not have anemia, "thin" macrocytes, "target" macrocytes, or acanthocytosis, unlike many persons hepatic disease such as chronic liver disease. Erythrocyte parameters in C282Y/C282Y probands did not differ significantly in the presence or absence of hepatomegaly, elevated serum concentrations of hepatic enzymes, or hepatic cirrhosis. Further, other persons with hemochromatosis previously reported, similar to our C282Y/C282Y probands, also had a normal mean Hct (41.6%; range 32–53% (n=30)) and an elevated mean MCV (99.8 fL; range 91–112 fL (n=20)). Before iron depletion therapy, 44% and 52% of our probands had values of MCV and MCH above the normal reference ranges, respectively. After treatment, 28% and 45% had elevated values of MCV and MCH, respectively. Because hemochromatosis is common, this disorder is a frequent cause of elevated "normal range" values of MCV, MCH, and "thick" macrocytosis among western Caucasians that is not generally recognized. As a result, many previously accepted "normal" ranges are really elevated due to the presence of hemochromatosis patients in the tested normal pool. The data reported herein is useful to correct the standard range values for such parameters such as MCV or MCH that are affected hemochromatosis.

Approximately 10% of diferric transferrin is usually present in the plasma of normal persons and this satiates the

TABLE 4

Erythrocyte Parameters in 94 Treated Hemochromatosis Probands.*

| HFE genotype†(n) | RBC, 10₆/uL | Hb, g/dL | Hct, % | MCV, fL | MCH, pg | MCHC, g/dL |
|---|---|---|---|---|---|---|
| C282Y/C282Y (60) | 4.38 ± 0.34 | 14.1 ± 1.1 | 41.5 ± 2.9 | 94.9 ± 5.1 | 32.2 ± 2.0 | 33.9 ± 1.2 |
| C282Y/H63D (8) | 4.89 ± 0.37 | 15.2 ± 4.0 | 45.3 ± 6.9 | 92.9 ± 2.3 | 31.0 ± 2.3 | 33.8 ± 1.2 |
| H63D/wt (5) | 4.66 ± 0.67 | 14.7 ± 2.3 | 43.9 ± 7.4 | 94.2 ± 2.4 | 31.5 ± 2.4 | 33.5 ± 0.7 |
| H63D/H63D (3) | 4.43 ± 0.49 | 13.7 ± 1.3 | 40.8 ± 2.8 | 92.3 ± 1.1 | 31.0 ± 1.1 | 33.6 ± 1.4 |
| wt/wt (6) | 4.53 ± 3.59 | 13.7 ± 1.4 | 40.4 ± 3.6 | 89.3 ± 5.1 | 29.9 ± 2.3 | 33.2 ± 1.0 |

*Data are displayed as mean ± 1 S.D. Probands were treated with therapeutic phlebotomy as described (15). In the first few weeks after the initiation of weekly phlebotomy therapy, transient increases in values of MCV attributed at a time when the serum ferritin concentration was 20–50 ng/mL. Pre-phlebotomy values of these probands are displayed in Table 3.
†C282Y, cDNA nucleotide 845 G→A; H63D, cDNA nucleotide 187 C→G; wt, wild-type (normal) HFE allele.

Diagnosis of Hemochromatosis

In C282Y/C282Y hemochromatosis probands, mean values of Hb, Hct, MCV, and MCH were 7.1–8.9% greater, on the average, than those of wt/wt normal control subjects. These changes occurred in association with a 1.8% increase in mean MCHC, and without a significant increment in RBC count. This represents an average of approximately five grams of additional circulating hemoglobin per proband (equivalent to ~170 mg of iron) than is found in wt/wt normal controls, based on a blood volume of five liters and the assumption that plasma volume is normal in persons with hemochromatosis. As in persons with iron deficiency, MCV and MCH were more sensitive than MCHC in detectiron requirements of erythropoiesis. However, transferrin saturation is typically elevated in untreated persons with hemochromatosis, including probands. Some hemochromatosis heterozygotes also have elevated values of transferrin saturation. After phlebotomy therapy, mean transferrin saturation values are lower but usually remain elevated. In our probands, mean MCV, MCH, and MCHC also decreased after phlebotomy therapy, but remained significantly elevated. Biochemical and electrophoretic characteristics of transferrin in hemochromatosis are normal, and there are no reports of possible mutations in the transferrin gene or its regulatory elements that could account for unusual cases of hemochromatosis. Thus, the increased transferrin saturation characteristic of hemochromatosis could cause increased iron uptake into developing erythroid cells by a transferrin-dependent mechanism.

Non-transferrin-bound iron (NTBI) occurs in the plasma of most untreated hemochromatosis patients, and is often detectable after iron depletion therapy. NTBI is also present in the plasma of some hemochromatosis heterozygotes who have normal transferrin saturation. Further, NTBI can enter erythroid cells via a transferrin-independent pathway, although the extent to which this mechanism functions in hemochromatosis is unknown. Pre-incubation of a wide variety of cell types with ferric ammonium citrate results in marked stimulation of $^{59}$Fe incorporation from $^{59}$Fe-transferrin at concentrations greater than those required for saturation of the transferrin receptor. However, this phenomenon has never been documented using erythroid cells. This nonetheless suggests that NTBI in the plasma of iron-overloaded patients may also promote increased loading of erythroid cells with iron derived from diferric transferrin in vivo.

In several extra-intestinal, non-erythroid cell types in hemochromatosis, transferrin receptor function and regulation appear to be normal. However, mRNA for transferrin receptor is inappropriately increased in the duodenum in hemochromatosis. A corresponding increase in erythroid cell surface transferrin receptor expression could explain increased transferrin-mediated iron uptake by erythroid cells in hemochromatosis. Interactions of transferrin receptor, transferrin, and mutant and wt HFE proteins observed in cultured cells could also explain some of the differences of iron absorption observed in persons with hemochromatosis and in normal subjects. Because HFE protein is not expressed in normal marrow erythroid cells or in K562 erythroleukemia cells, interaction of intracellular HFE with transferrin and transferrin receptor may not facilitate iron transport in erythroid cells. However, a role for soluble HFE protein in modifying erythroid cell iron uptake cannot be excluded. A divalent metal cation transporter (Nramp2, DCT1, DMT1) probably accounts for the increased entry of iron into enterocytes in hemochromatosis. The same transporter removes transferrin-bound iron from endocytic vesicles in erythroid cells, and functions abnormally in the presence of mutant HFE protein or other factors that occur in hemochromatosis.

C282Y/C282Y probands who were HLA-A3-negative had higher mean MCH and MCHC values than HLA-A3-positive probands, and some probands without detectable HFE mutations also had abnormal erythrocyte parameters. This indicates that genetic factors other than HFE also influence peripheral blood erythrocyte parameters in hemochromatosis.

Other embodiments are within the following claims.

What is claimed is:

1. A method of diagnosing hemochromatosis or a predisposition thereto in a mammal, comprising determining a mean corpuscular volume (MCV) value of a blood sample from said mammal, wherein an increase of at least 5% compared to a normal control value indicates that said mammal has hemochromatosis or is predisposed to developing hemochromatosis.

2. The method of claim 1, wherein said increase is at least 10% greater compared to a normal control value.

3. The method of claim 1, wherein an erythrocyte parameter of said mammal is not indicative of anemia.

4. The method of claim 3, wherein said erythrocyte parameter is red blood cell count (RBC), hematocrit (Hct) or hemoglobin concentration (Hb).

5. A method of diagnosing hemochromatosis or a predisposition thereto in a mammal, comprising determining a mean corpuscular volume (MCV) value of a blood sample from said mammal, wherein a value of at least 80 fL indicates that said mammal has hemochromatosis or is predisposed to developing hemochromatosis.

6. The method of claim 5, wherein said value is at least 85 fL.

7. The method of claim 5, wherein said value is in the range of 90–102 fL.

8. The method of claim 5, wherein an erythrocyte parameter of said mammal is not indicative of anemia.

9. The method of claim 8, wherein said erythrocyte parameter is a red blood cell count (RBC), hematocrit (Hct) or hemoglobin concentration (Hb).

10. A method of diagnosing hemochromatosis or a predisposition thereto in a mammal, comprising determining a mean corpuscular hemoglobin (MCH) value of a blood sample from said mammal, wherein an increase of at least 5% compared to a normal control value indicates that said mammal has hemochromatosis or is predisposed to developing hemochromatosis.

11. The method of claim 10, wherein said increase is at least 10% greater compared to a normal control value.

12. The method of claim 10, wherein an erythrocyte parameter of said mammal is not indicative of anemia.

13. The method of claim 12, wherein said erythrocyte parameter is a red blood cell count (RBC), hematocrit (Hct) or hemoglobin concentration (Hb).

14. A method of diagnosing hemochromatosis or a predisposition thereto in a mammal, comprising determining a mean corpuscular hemoglobin (MCH) value of a blood sample from said mammal, wherein a value of at least 26 pg indicates that said mammal has hemochromatosis or is predisposed to developing hemochromatosis.

15. The method of claim 14, wherein said value is at least 28 pg.

16. The method of claim 14, wherein said value is in the range of 30–35 pg.

17. The method of claim 14, wherein an erythrocyte parameter of said mammal is not indicative of anemia.

18. The method of claim 17, wherein said erythrocyte parameter is a red blood cell count (RBC), hematocrit (Hct) or hemoglobin concentration (Hb).

* * * * *